United States Patent [19]

Wolfinbarger, Jr.

[11] Patent Number: 5,531,791
[45] Date of Patent: Jul. 2, 1996

[54] COMPOSITION FOR REPAIR OF DEFECTS IN OSSEOUS TISSUES, METHOD OF MAKING, AND PROSTHESIS

[75] Inventor: Lloyd Wolfinbarger, Jr., Norfolk, Va.

[73] Assignee: Bioscience Consultants, Norfolk, Va.

[21] Appl. No.: 95,020

[22] Filed: Jul. 23, 1993

[51] Int. Cl.⁶ .............................. A61F 2/28; A61K 35/32; A61K 37/12
[52] U.S. Cl. ................................ 623/16; 623/66; 623/11; 523/113; 523/115; 530/356; 424/422; 424/423
[58] Field of Search ................................. 623/1, 11, 12, 623/16, 66; 435/68.1; 530/356, 416, 417; 424/95, 177, 422, 423; 523/115, 113

[56] References Cited

U.S. PATENT DOCUMENTS

| | | |
|---|---|---|
| 3,742,955 | 7/1973 | Battista . |
| 3,810,473 | 5/1974 | Cruz, Jr. et al. . |
| 3,949,073 | 4/1976 | Daniels et al. . |
| 4,140,537 | 2/1979 | Luck et al. . |
| 4,223,360 | 12/1980 | Luck et al. . |
| 4,314,380 | 2/1982 | Miyata et al. . |
| 4,394,370 | 7/1983 | Jeffries . |
| 4,412,947 | 11/1983 | Cioca . |
| 4,424,208 | 1/1984 | Wallace et al. . |
| 4,430,760 | 2/1984 | Smestad . |
| 4,434,094 | 2/1984 | Seyedin et al. . |
| 4,440,750 | 4/1984 | Glowacki et al. . |
| 4,488,911 | 12/1984 | Luck et al. . |
| 4,515,637 | 5/1985 | Cioca . |
| 4,557,764 | 12/1985 | Chu . |
| 4,563,350 | 1/1986 | Nathan et al. . |
| 4,578,067 | 3/1986 | Cruz, Jr. . |
| 4,582,640 | 4/1986 | Smestad et al. . |
| 4,600,533 | 7/1986 | Chu . |
| 4,627,982 | 12/1986 | Seyedin et al. . |
| 4,642,117 | 2/1987 | Nguyen et al. . |
| 4,655,980 | 4/1987 | Chu . |
| 4,687,763 | 9/1987 | Wurtman . |
| 4,689,399 | 7/1987 | Chu . |
| 4,725,671 | 2/1988 | Chu et al. . |
| 4,774,227 | 9/1988 | Piez et al. . |
| 4,774,228 | 9/1988 | Seyedin et al. . |
| 4,774,322 | 9/1988 | Seyedin et al. . |
| 4,776,890 | 10/1988 | Chu . |
| 4,789,663 | 12/1988 | Wallace et al. . |
| 4,795,467 | 1/1989 | Piez et al. . |
| 4,803,075 | 2/1989 | Wallace et al. . |
| 4,806,523 | 2/1989 | Bentz et al. . |
| 4,810,691 | 3/1989 | Seyedin et al. . |
| 4,816,442 | 3/1989 | McPherson et al. . |
| 4,843,063 | 6/1989 | Seyedin et al. . |
| 4,863,475 | 9/1989 | Andersen et al. . |
| 4,863,732 | 9/1989 | Nathan et al. . |
| 4,865,602 | 9/1989 | Smestad et al. . |
| 4,888,366 | 12/1989 | Chu et al. . |
| 4,950,483 | 7/1990 | Ksander et al. . |
| 4,968,590 | 11/1990 | Kuberasampath et al. . |
| 4,992,226 | 2/1991 | Piez . |
| 5,001,169 | 3/1991 | Nathan et al. . |
| 5,008,240 | 4/1991 | Bentz et al. . |
| 5,011,691 | 4/1991 | Opperman et al. . |
| 5,024,841 | 6/1991 | Chu et al. . |
| 5,035,715 | 6/1991 | Smestad et al. . |
| 5,071,351 | 12/1991 | Green, Jr. et al. . |
| 5,073,373 | 12/1991 | O'Leary et al. . |
| 5,108,436 | 4/1992 | Chu et al. . |
| 5,110,604 | 5/1992 | Chu et al. . |
| 5,123,925 | 6/1992 | Smestad et al. . |
| 5,162,114 | 11/1992 | Kuberasampath et al. . |
| 5,162,430 | 11/1994 | Rhee et al. . |
| 5,171,574 | 12/1992 | Kuberasampath et al. . |
| 5,207,710 | 5/1993 | Chu et al. . |
| 5,219,576 | 6/1993 | Chu et al. . |
| 5,246,457 | 9/1993 | Piez et al. . |
| 5,250,302 | 10/1993 | Oppermann et al. . |
| 5,258,029 | 11/1993 | Chu et al. . |
| 5,258,494 | 11/1993 | Oppermann et al. . |
| 5,264,214 | 11/1993 | Rhee et al. . |
| 5,266,683 | 11/1993 | Oppermann et al. . |

FOREIGN PATENT DOCUMENTS

| | | |
|---|---|---|
| 1142430 | 3/1983 | Canada . |
| 0030583 | 6/1981 | European Pat. Off. . |
| 0495284 | 7/1992 | European Pat. Off. . |
| 58-58041 | 4/1983 | Japan . |
| 9218142 | 10/1992 | WIPO . |

OTHER PUBLICATIONS

Toole et al., "Hyaluronate Production and Removal During Corneal Development in the Chick", Developmental Biology 26, 28–35, 1971.

Docherty et al., "Glycosaminoglycans facilitate the movement of fibroblasts through three-dimensional collagen matrices", Journal of Cell Science 92, 263–270, 1989.

Tsunenaga et al., "Effect of Hyaluronate on Physiochemical and Biological Properties of Collagen Solution which could be used as Collagen Filler", Connective Tissue Research, vol. 28, 113–123, 1992.

Beghe et al., "Lyophilized Non-Denatured Type-1 Collagen (Condress) Extracted from Bovine Achilles' Tendon and Suitable for Clinical Use", Int. J. Tiss. Reac. XIV(Suppl.) 11–19, 1992.

Klebe, "Isolation of a Collagen–Dependent Cell Atachment Factor", Nature vol. 250, 248–251, Jul. 19, 1974.

Ehrmann et al., "The Growth of Cells on a Transparent Gel of Reconstituted Rat–Tail Collagen", Journal of the National Cancer Institute, vol. 16, No. 6, 1375–1403, Jun., 1956.

Primary Examiner—David Isabella
Attorney, Agent, or Firm—Klima & Hopkins

[57] ABSTRACT

A biocompatible collagen/demineralized human bone composite material, method for making the same, and prostheses employing the same are disclosed, wherein the composite material may be formulated into a fluid injectable, gel or rehydratable freeze dried paste. The resultant products can be used either alone or combined with a prosthetic device as an osteoinductive/osteoconductive material.

27 Claims, No Drawings

COMPOSITION FOR REPAIR OF DEFECTS IN OSSEOUS TISSUES, METHOD OF MAKING, AND PROSTHESIS

BACKGROUND OF THE INVENTION

1. Field of the Invention

This invention relates to a biocompatible, osteoinductive/osteoconductive, collagen/demineralized human bone composite material that may be used in a fluid injectable or rehydratable freeze-dried paste form, and to a process for making this material. The composition possesses the attributes of being deliverable as a mixture in a fluidized state or as a mixture in a gel state, of being compatible with tissues surrounding the site(s) of its application, of promoting cellular infiltration from adjacent osseous tissues following application, and of possessing osteoinductive/osteoconductive properties such that it will ultimately be remodeled and the application site returned to a mineralized, hard tissue.

2. Discussion of Background Information

The induced formation of new bone through the use of various matrix material has been discussed in the past. In this regard, various matrix materials and various combinations of the matrix materials have been formulated into implantable, as well as injectable forms.

One group of technology uses collagen, demineralized bone or a combination of the two to form implantable sponges, bandages or prostheses. For instance, U.S. Pat. No. 4,394,370 describes the fabrication of a sponge suitable for in vivo implantation in osseous defects. In particular, the sponge is fabricated using a complex of reconstituted collagen and demineralized human bone particles or reconstituted collagen and a solubilized bone morphogenetic protein. Specifically, the sponge described in U.S. Pat. No. 4,394,370 utilizes more than 50% of nonhuman microcrystalline collagen in conjunction with demineralized bone powder (particle size less than 75 microns) and glutaraldehyde to cross-link the collagen.

U.S. Pat. No. 4,412,947, describes a process for preparing a porous collagen sheet material used for wound healing. The device is an absorbent dressing having a bulk density of 0.005 to 0.0065 g/cm$^3$ made by freeze-drying a dispersion of particulate xenogeneic collagen in a weak aqueous organic acid solution.

Another example of an implant is U.S. Pat. No. 5,110,604 which describes a collagen implant useful as a wound healing matrix or sustained release depot for administration of bioactive agents. The implant utilizes a commercially available atelopeptide bovine skin collagen, that is chemically cross-linked. Moreover, the invention provides for the addition of "bioactive additives" such as fibroblast growth factor.

Other patents describing nonhuman collagen sponges are U.S. Pat. Nos. 3,742,955, 3,810,473, 4,515,637, and 4,578,067.

Another group of technology uses collagen and a mineral component to form the implantable material. For example, U.S. Pat. No. 5,001,169 describes a composition suitable for inductive bone implants. The composition comprises a mixture of a purified form of osteogenic factor with a carrier. In particular, the carrier comprises at least 75% of a mineral component such as various forms of calcium phosphate—i.e., hydroxyapatite or tricalcium phosphate—and the rest is fibrillar collagen, non-fibrillar collagen or a combination of the two. The resulting implants are sufficiently hypoimmunogenic to be effective when implanted in xenogeneic hosts.

Additionally, U.S. Pat. No. 5,123,925 describes a formable composition comprised of 2–40% of reconstituted fibrillar atelopeptide collagen and 60–98% calcium phosphate mineral. This patent discusses use of gamma irradiation on collagen/mineral mixtures to improve both biological and handling properties where cross-linking of the mixture by irradiation was enhanced.

Moreover, U.S. Pat. No. 4,314,380 utilizes a mineral backbone, prepared by the treatment of animal bone to remove all organic materials, which is then coated with an atelopeptide collagen. In addition, Japanese Application J58/058041, published Apr. 6, 1983 discloses a spongy porous calcium phosphate material having pores treated with atelopeptide collagen. Further, European patent No. 0 030 583, published Jun. 24, 1981, discloses use of a collagen fleece in admixture with hydroxyapatite in bone repair. The collagen material is a commercial product obtained from animal hides by proteolytic digestion. Finally, U.S. Pat. No. 4,992,226 provides for a process for coating the pores of a mineral matrix with collagen by pumping collagen through the molded matrix. The resulting coated matrix could be used as a prosthesis in bone repair (see also U.S. Pat. No. 4,795,467.)

Yet another group of patents discloses the bone forming material as being injectable. For example, U.S. Pat. No. 4,424,208 discloses an implant material comprised of a dispersion of solid elastic particles of cross-linked atelopeptide collagen and reconstituted atelopeptide collagen fibers in a physiologically aqueous carrier. While this material is injectable through medium gauge needles, its extrusion and intrusion properties are poor.

Another patent disclosing injectable forms of various collagen and bone products to induce bone formation is U.S. Pat. No. 4,440,750. This patent describes the use of a plastic dispersion of demineralized bone powder and reconstituted native nonhuman atelopeptide collagen fibers or tropocollagen in a continuous aqueous phase. The continuous phase has a substantially physiologic pH and ionic strength and is said to be used in repair or in reconstruction of bone by injection or implantation at the repair or reconstruction site. The patent describes the collagen as either retaining its telopeptide or preferably the collagen can be without its telopeptide. Further, the collagen is prepared from the skin of a variety of mammalian sources (xenogeneic), and therefore the collagen is composed of type I and type III xenogeneic collagen. Moreover, the demineralized bone powder is also xenogeneic (preferably bovine or porcine), and is demineralized via a process which provides a heterogeneous demineralized bone product.

Still a further patent that discloses an injectable material is U.S. Pat. No. 4,789,663 which describes a method of repairing bone defects using a suspension containing purified atelopeptide, reconstituted, fibrillar skin collagen or bone collagen powder or mixtures thereof. In this regard, the suspensions provide a matrix for conductive growth of bone into the defect. In addition, the patent describes the formation of the skin collagen into freeze dried "mats". The patent describes the use of bone derived collagen produced from demineralized bone, and its collagen component is primarily type I collagen. In particular, the collagen is removed from the bone using a non-collagenase protease, such as trypsin, and then formed into a powder. The described method of collagen preparations, i.e. using a protease such as trypsin, has the effect of destroying factors such as bone morphogenetic proteins (BMP) responsible for inductive repair osteogenesis, as well as cleaving the telopeptides from the collagen which is necessary for intramolecular cross-linking of type I collagen.

An additional example of an injectable aqueous suspension of biomaterials is disclosed in U.S. Pat. No. 4,803,075. This patent describes a collagen which is cross-linked, and contains a biocompatible fluid lubricant such as glycogen, or maltose, and it is disclosed that the inclusion of the lubricant significantly improved the intrusion of the suspension into soft tissue.

A further example of an injectable composition for inductive bone repair is U.S. Pat. No. 4,863,732, which discloses the use of aqueous suspensions of fibrillar atelopeptide collagen, prepared from a nonhuman source, and osteogenic factor(s) isolated from demineralized bone. Even more specifically, the osteogenic factor(s) are isolated using dissociative solvents and purified by gel filtration column chromatography (S-200) to obtain the low molecular weight (<35,000 daltons) proteins.

A still further injectable composition is U.S. Pat. No. 5,073,373 which describes a flowable, injectable, demineralized bone powder composition provided for use in surgical bone repair. The composition utilizes a biocompatible liquid synthetic organic material as the carrier for the demineralized bone. In this regard, liquid refers to either organic materials which, in the pure or highly concentrated state and at ambient temperature, are flowable liquids; or organic materials which, in the pure or concentrated state and at ambient temperature, are normally solid, but dissolved in a suitable solvent, such as water, ethanol, etc., can be provided in liquid form. In particular, suitable organic materials (carriers) include liquid polyhydroxy compounds and their esters, polysaccharides, surface active agents, and the like. Specific polyhydroxy compounds of the foregoing type include glycerol, as well as its monoesters and diesters derived from low molecular weight carboxylic acids, e.g., monacetin and diacetin. In particular, glycerol is the preferred liquid organic carrier.

U.S. Pat. No. 5,073,373 further discloses that a variety of substances can be introduced into the demineralized bone particles used in this preparation and include, for example, antibiotics, amino acids, vitamins, angiogenic drugs, collagen lattices, biologically active components such as bone morphogenetic protein (BMP), and mesenchymal elements.

European Patent number 0 495 284 A1 also describes an injectable composition as a surface adherent osteogenic composition derived from demineralized bone. In this regard, the demineralization of bone is further processed by acid-promoted cleavage of the bone collagen matrix with 2N hydrochloric acid at elevated temperatures, most preferably from about 40° C. to about 55° C. The acid degraded bone derived collagen is obtained in a denatured state wherein the fibrillar structure of the collagen has been altered.

The patent discloses that the collagen preparation can be used as the carrier for a host of medically/surgically useful substances including insoluble solids such as demineralized bone powder.

Additional documents disclosing injectable solutions of biomaterials include U.S. Pat. Nos. 3,949,073, and 4,582,640.

SUMMARY OF THE INVENTION

It is an objective of the invention to provide a flowable composite material of a collagen carrier/matrix and demineralized bone powder for use in bone repair and growth.

In this regard, it is an object of the invention to provide, as the carrier/matrix component of the composition, a biocompatible liquid form of human collagen which will provide a sufficiently viscous gel-like matrix so as to be injectable through large gauge applicators yet remain largely at the site of application. Moreover, the collagen carrier should also promote cellular infiltration by providing a molecular matrix for cell migration and retain the demineralized bone particles at the site of application without being cytotoxic.

Another object of this invention is to provide a collagen that contains parallel bundles that are anisotropic and essentially type I collagen. In this regard, type I collagen (found in ligaments, tendons and bones) is preferred over type III collagen (found in skin) because type I collagen lacks two adjacent cysteines at the C-terminal end of the triple-helix. Moreover, the type I collagen should retain its telopeptide because type I collagen in its atelopeptide form is incapable of forming inter-chain disulfide cross-links.

Moreover, the collagen must be easily isolated from the mild acid solution, for example by precipitation in a final concentration of sodium chloride (NaCl) of 1.5 to 3.5M, and easily dialyzed from either the acid or salt solutions and further easily sterilizable using gamma radiation doses between 0.5 and 1.5 Mrad, without causing degradation of the collagen. An additional objective is that the isolated collagen is easily stored, easily reconstituted after storage, and suitable for clinical use.

An even further object of the invention is that the reconstituted collagen is able to bind large and small molecular weight macromolecules, including hyaluronate which is known to play a role in cell migration (Toole, B. P. and Trelstad, R. L. 1971, Develop. Biol. 26:28–35; Docherty, R. et al. 1989, J. Cell. Sci. 92:263–270) and has been implicated in facilitating fibril formation which promotes gelation of a liquified form of collagen (Tsunenaga, M. et al. 1992. Connect. Tiss. Res. 28:113–123.).

A further object of the invention is that the collagen provide excellent histocompatibility and elicit minimal antibody formation or immunological rejection.

Even further, it is an object of the invention that the demineralized bone powder contain physiologically active levels of a factor, BMP, which can be solubilized from demineralized bone and induce osteogenesis.

A yet further object of the invention is that both the bone material and the collagen be obtained economically, come from the same donor source, and be safe.

In keeping with these and related objectives of the invention, there is provided a composite material for the promotion of allogenic bone growth and repair comprising demineralized bone powder, and essentially type I telopeptide containing collagen derived from tendons and ligaments. Moreover, the tendons and ligaments, from which the essentially type I telopeptide containing collagen is be derived, can be obtained from a human source. Further, both the demineralized bone powder and essentially type I telopeptide containing collagen can be obtained from the same human source.

It is also provided that the composite material comprises about 0.25 to 40 weight percent essentially type I telopeptide containing collagen.

Further, the type I telopeptide containing collagen is derived from a collagen source by a process comprising extracting the collagen from the collagen source in dilute acid, then precipitating the collagen from the acid solution, followed by washing of the collagen precipitate. In this respect, a dilute acid is used in order to minimize changes in the structural integrity of the collagen caused by the isolation proceedure. In particular, a dilute organic acid is used such as acetic acid, lactic acid, malic acid, citric acid, glutaric acid or proprionic acid, but preferably acetic acid. Furthermore, the pH of the dilute organic acid is in the range of pH 3 to 4.

In addition, the derivation of the collagen includes the additional steps of resolubilization of the washed collagen precipitate, followed by dialysis of the resolubilized washed collagen precipitate against isotonic saline. Moreover, the steps of washing the collagen precipitate, then resolubilizing the washed collagen precipitate, followed by dialysis of the resolubilized washed collagen precipitate against isotonic saline can be repeated from 2 to 6 times.

It is further provided that the composite material contain about 20 to 90 weight percent demineralized bone powder. Even further, a preferred composition comprises about 30 to 50 weight percent demineralized bone powder.

It is still further provided that the composite material use a demineralized bone powder, that is widely and reliably available from a tissue bank, such as LifeNet Transplant Services, Virginia Beach, Va., with a particle size of from about 125 millimicrons to about 2 millimeters, and more preferably, demineralized bone powder with a particle size in the range of from about 125 microns to about 500 millimicrons. A further preferred size for the particle size for the demineralized bone is from about 250 microns to about 710 millimicrons, and a yet additional preferred particle size for the demineralized bone powder is from about 710 microns to about 2 millimeters.

It is yet additional provided that the composite material is flowable, injectable, a gel, or a paste.

Furthermore, the composition provides that additional elements may be included in the composite material and are selected from the group consisting of bioactive compounds, antibiotics, antiviral agents, antitumor agents, immunosuppressive agents, permeation enhancers, nucleic acids, mesenchymal elements, gelation enhancing compounds and autogenously derived osteoblast cells. In this regard, the bioactive compound is at least one member selected from the group consisting of BMP, transforming growth factor beta, fibroblast growth factor, insulin, and platelet derived growth factor. In this regard, it is provided that the antibiotic agent comprise penicillin; the antiviral agent comprise a detergent, such as Triton X-100, Nonidet P-40, and Brij-35; the antiviral agent comprise a peroxide generating agent; the immunosuppressant agent comprise bovine intestinal alkaline phosphatase; the permeation enhancer comprise a fatty acid ester, such as a monoester of polyethylene glycol selected from the group consisting of laurate, myristate and stearate; and the gelation enhancing compound comprise a glycosamino glycan selected from the group of consisting of hyaluronic acid, chondroitin sulfate, or dermatin sulfate.

It is even further provided that the invention includes a method of preparing a composition for the promotion of allogenic bone growth and repair comprising demineralizing human bone powder, extracting essentially type I telopeptide containing collagen, and combining the demineralized bone powder and the extracted essentially type I telopeptide containing collagen. In this regard, a source for the demineralized bone powder, and the essentially type I telopeptide containing collagen is a human source, and in some cases the source for both components is the same human source.

Yet additionally a method is provided for preparing the composite material wherein the material is applied to a prosthetic device, to facilitate osteoconduction, and/or osteoinduction of native bone around the implant in order to build a stronger and more compatible association between the implant and the native bone. In addition, another provision of the composition is an implantable bone prosthesis comprising a substrate formed of a biocompatible metal, ceramic or composite; and at least a partial coating comprising demineralized bone particles and essentially type I telopeptide containing collagen. Moreover, the composite material that is coating at least part of the prosthesis can in some cases be derived from the same human source.

A yet additional provision of the composition is a method of preparing a composite material for the promotion of allogenic bone growth and repair comprising mixing the demineralized bone particles with the essentially type I telopeptide containing collagen; wherein the step of preparing essentially type I telopeptide containing collagen comprises, first selecting a source from the group consisting of ligaments, tendons and mixtures thereof, then physically pulverizing the source, then washing the source, and finally extracting the collagen in dilute solutions of acid.

It is provided that the demineralized bone powder and collagen carrier/matrix can be obtained and prepared as needed, and, preferably with the components of the composite obtained from the same human donor source. In this regard, it is provided that the composite material and the means for applying the composite material to a bone defect site may be provided in the form of a unitary kit. Alternatively, the demineralized bone powder and the collagen carrier/matrix, again preferably from the same donor source, can be prepared under sterile conditions and stored separately, or mixed and stored together, for later use. Optionally, the storage of the two components can be within the means, such as a syringe, which will be used to apply the composition to the bone defect site.

DETAILED DESCRIPTION OF THE PREFERRED EMBODIMENTS

The formulation of the preferred embodiment of the present invention is formed in a highly reproducible fashion. In this regard, the process for producing the ground demineralized human bone is described in U.S. application Ser. No. 07/664,675, which is hereby incorporated by reference in its entirety. Specifically, the preferred demineralization process begins by pulverizing the donor human bone to a particle size range of 1 to 2 mm. The pulverized human bone is then treated by being mixed in an ethanol solution of 70 to 100% ethanol, volume to volume, in deionized/distilled water to effect a "defatting" of the bone. The preferred concentration of ethanol is 100% (absolute), because of its greater capacity for solubilization of less polar solutes such as lipids.

The defatted bone particles are then freeze-dried and further ground to smaller particle sizes. In this regard, the particles are sized, using commercially available sieving devices, to a particle size range of approximately 150 microns to 2 millimeters, with the preferred particle size range of 250 microns to 710 microns. Further preferred embodiment has a particle size range of 125 to 500 microns. Yet an additional preferred embodiment has a particle size of 710 microns to about 2 millimeters.

The bone particles are then washed with an ethanol solution ranging from 70% to 100%, with the preferred concentration being 70% to 95%. The ethanol solution is pumped over the bone particles at an approximate flow rate of 1 ml per minute to effect a continual change of solvent and removal of extracted ethanol soluble solutes, for example lipids, from the bone particles.

An alternative ethanol solution may include ionic and nonionic detergents such as sodium dodecyl sulfate, polyglycol ethers such as Nonidet P-40, (a registered trademark of Shell), a series of polyoxyethylene ethers of fatty alcohols such as cetyl, stearyl, and oleyl alcohols (Brij-35), Polyethylene Glycol p-Isooctylphenyl Ether (Triton X-100), etc., in concentrations ranging from 0.002 weight percent to 2 weight percent, with a preferred concentration range of 0.02 to 0.2 weight percent. This processing step provides the additional advantage of inactivation of potential viral contaminants such as the HIV and hepatitis viruses.

Extraction of ethanol soluble solutes, most especially lipids, may be monitored spectrophotometrically for completion of the extraction process. Then, when the extraction is completed, alternative solutions of either deionized/distilled endotoxin-free water or a solution of hydrochloric acid, may be pumped through the demineralization device to both remove the ethanol and effect subsequent processing of the bone particles.

Alternative solutions are provided because deionized/distilled water is sometimes used to flush the ethanol/lipid solution from the device prior to addition of the acid solution in order to permit a more accurate assessment of the time taken to demineralize the bone particles. In this regard, the prewash with deionized/distilled water prevents the removal of additional lipid components from the bone particles that may occur when the ethanol solution is washed out using acid solution alone.

With regard to the hydrochloric acid solution used in the demineralization of the bone particles, the range of concentrations of the solution is from pH 1 and pH 2 with the preferred concentration ranging from 0.5 to 0.6N. This acid solution is pumped over the bone particles at a rate sufficient to maintain the pH of the eluent below pH 3.0.

The demineralization process can be monitored by measuring the solution after it has passed over the bone particles for either the concentration of calcium ion, using a calcium specific electrode, or for the pH, using a standard pH probe. An end point has been reached when the calcium ion concentration or pH of the solution after it has passed over the bone particles has declined to a stable value such that either the calcium ion concentration or pH of the eluent solution approximates the calcium ion concentration or pH of the solution before it has passed over the bone particles.

In this regard, demineralized bone has been defined by the American Association of Tissue Banks Standards as containing less than 5% by weight residual calcium. However, typically, when the calcium ion concentration or pH of the eluent, following the presently described process, has declined to a stable value, the bone particles contain less than 0.1% by weight residual calcium.

When demineralization of the bone particles is completed, the acid solution is removed from the bone particles by pumping deionized/distilled endotoxin-free water over the bone particles until the pH of the eluent approximates the pH of the water before it is pumped over the bone particles. In this regard, the pH of deionized/distilled water approximates pH 5.5 to 6.5 when measured in the presence of ionic strength adjuster, such as potassium chloride.

For purposes of the present invention, an isotonic saline solution may be substituted for the deionized/distilled water in order to hydrate the demineralized bone powder in an isotonic solution appropriate to human cells and serum. Moreover, in the event the demineralized bone powder is to be used immediately, and combined with the collagen carrier/matrix component of the invention, isotonic saline should be used to remove any acid solution from the bone particles.

If the demineralized bone powder is to be used later, it may be conveniently stored by freeze-drying to maintain the activity of contained bioactive components, such as BMP. However, if the demineralized bone powder is to be freeze-dried, for later use, the acid solution from the demineralization step should be removed using deionized/distilled endotoxin-free water, in order to remove elevated levels of salts in the freeze-dried bone.

The collagen carrier/matrix of the composite material herein described is obtained from human ligament/tendon tissues. In this regard, the collagen comprises primarily type I collagen, similar to that collagen type normally found in bone. Therefore, collagen containing essentially type I telopeptide is employed in the instant invention because it is capable of forming natural interstrand cross-links in the telopeptide region when reformed into the composite material herein described. Further, type I collagen, as described in this invention, has been shown to increase fibroblast migration and proliferation (Ehrmann, et al. (1956) J. Natl. Canc. Inst. 16:1475–1490) and to also increase the rate and extent of cell attachment (Klebe, (1974) Nature. 250:248–251).

The extraction procedures described herein are essentially similar to those procedures described by Beghe, F., et al. 1992. Int. J. Tiss. Reac. XIV (suppl) 11–19, which is hereby incorporated by reference in its entirety. In this regard, the disclosed procedures are utilized because they are so mild that noncollagenous proteins, such as hyaluronic acid and other proteoglycans, present in the tissues to be used in the preparation of the collagen carrier/matrix, may be expected to be present in the prepared collagen carrier/matrix.

Preferably, the ligament/tendon tissue may be obtained from the same source, i.e., the same human cadaveric donor from which the bone, used in the preparation of the demineralized bone powder, is processed. This significantly reduces the risk of contamination of the end product by viruses such as HIV and hepatitis. The ligament/tendon tissues are cut into small pieces, triturated and washed with distilled/deionized endotoxin-free water and isotonic saline, and then extracted in an aqueous solutions of organic acid such as acetic acid, lactic acid, malic acid, citric acid, glutaric acid or proprionic acid. In this regard the preferred organic acid is acetic acid. The concentration of acetic acid may range from 0.05M to 0.5M and the extraction time will approximate 24 hours at room temperature (20° C. to 24° C.). In order to maximize recovery of collagen, the extracted tissue may be reextracted with acetic acid solution a second time and the extracts are then combined.

The solubilized collagen contained in the extract solution may be precipitated by the addition of sodium chloride to the extract solution until the final concentration of sodium chloride is 1M to 2.5M, with the preferred concentration being 2.5M. The precipitated collagen may be washed with deionized/distilled endotoxin-free water and resolubilized in 0.05 to 0.5M acetic acid in water.

This process of precipitation, washing, and resolubilization provides a method for the removal of salt precipitable, acetic acid soluble small molecular weight components, and the process can be repeated until the desired purity is achieved. Repeating these steps as many as six times provides a very pure product with a high yield. It is preferred that three repetitions produces the most effective product in terms of yield and of purity of collagen. At the point of desired purity, the collagen may finally be dialyzed against isotonic saline and the concentration of collagen protein determined using standard protein determination assays.

For preparation of the composite material, the human collagen carrier/matrix and the ground demineralized human bone are added together. The concentration of the collagen carrier/matrix may range from 0.25% to 40%, by weight, depending on the desired viscosity and gelation characteristics of the desired mixture, with the preferred concentration of the collagen carrier/matrix being 0.5% to 4%, by weight. The concentration of demineralized bone in the collagen carrier/matrix may range from 20% to 90%, by weight, of the total composite, with the preferred concentration of from 30% to 50%, by weight.

Optional components may also be added to the composition, including, but not limited to, bioactive compounds, such as BMP, transforming growth factor beta, fibroblast growth factor, insulin, and platelet derived growth factor; antibiotics; antiviral agents such as detergents (for example Triton X-100, Nonidet P-40, Brij-35, etc.) or peroxide generating agents such as Exact (a trademarked product marketed by ExOxEmis, Inc., San Antonio, Tex.), etc.; antitumor agents; immunosuppressants; permeation enhancers (for example fatty acid esters such as the laurate, myristate and stearate monoesters of polyethylene glycol); nucleic acids; mesenchymal elements; gelation enhancing compounds such as hyaluronic acid, chondroitin sulfate, dermatin sulfate, or similar glycosamino glycans; and autogenously derived osteoblast cells for use in making the composite material osteogenic. In this respect, the invention includes other equivalent optional components readily known to those in the art.

To facilitate clinical usage of the invention, the individual components may be packaged separately in different forms and reconstituted and combined at the time of usage. Alternatively, the individual components may be added together and then packaged, as a premixed format. In particular, the premixed format provides the advantage of requiring minimal preparation by the individual clinician at the time of usage.

The premixed format would include the sterile composite material in a form suitable for application to a bone defect site employing any suitable means, e.g., a syringe, spatula, etc. For example, the sterile composition could be provided in a 1 to 5 cc syringe, equipped with a large gauge delivery tube of appropriate length and inside diameter. In this regard, a delivery tube with an inside diameter of not less than 1 mm is appropriate for the injection delivery into the surgical site for the preferred compositions.

For on-site preparation, the human collagen carrier/matrix and human demineralized bone may be provided in freeze-dried aliquots and rehydrated just prior to being combined for use in clinical applications. On-site preparation would have the advantage of increasing the ability to vary the concentrations and quantities of the collagen carrier/matrix and demineralized bone powder used in preparation of the composite material as well as permitting addition of optional components at the discretion of the clinician.

The following examples illustrate preparations of the flowable demineralized bone powder in a collagen carrier/matrix according to the instant invention.

EXAMPLE I

Allogenic bone and ligament/tendon tissues obtained from a human cadaver were procured and returned to the processing facility under sterile conditions. Donor histories, personal and medical, were obtained following accepted standards of the American Association of Tissue Banks. Microbiological tests were performed following FDA guidelines for testing for sterility of products.

The tissues were cleaned of excess unwanted tissues and used in the preparation of collagen carrier/matrix and demineralized bone powder. The ligament/tendon tissues were minced and extracted in 0.5M acetic acid, and the collagen present in the extract solution was precipitated by the addition of sodium chloride, at a 2.5M final concentration. The collagen carrier/matrix was prepared by dialysis against isotonic saline to remove excess salts and acetic acid and the concentration of collagen adjusted to 1% by weight.

The ground demineralized bone powder was prepared by impact fragmentation, followed by freeze-drying, and finally the particles were sized using mesh sieves. A particle size range of 250 to 710 millimicron was utilized.

In order to prepare the composite material, the freeze dried demineralized bone powder was rehydrated in isotonic saline, and added to the 1% collagen carrier/matrix until the final concentration of the bone in the composite material was 50% by weight. One milliliter aliquots of the composite material were added to 1 cc syringes equipped with a delivery tube and packaged into sterile peel pouches such that the inner peel pouch containing the syringe containing the composition is sterile and ready for delivery to the operating field.

EXAMPLE II

The allogenic demineralized bone and ligament/tendon tissues was prepared in the same way as is described in Example I. However, in this example Bovine intestinal alkaline phosphatase, at concentrations of 15 mg per gram of composition was added as an optional ingredient, for the purpose of eliminating the inflammatory response to the graft material, accelerate the formation of new bone at the site of application, and slow the resorption of graft materials.

In addition, the optional ingredient penicillin (10,000 to 30,000 units per gram of composition) was added. The antibiotic additive serves to reduce infections at the site(s) of application, particularly when used in the oral cavity for treatment of periodontal gum disease.

Aliquots (1 ml) of the mixture of demineralized bone powder and collagen carrier/matrix was added to 1 cc syringes equipped with a delivery tube and packaged into sterile peel pouches such that the inner peel pouch containing the syringe with inventive composition is sterile and ready for delivery to the operating field.

EXAMPLE III

The human allogenic bone and ligament/tendon tissue was processed in the same way as in Example I. However, in this example the collagen carrier/matrix was prepared for storage by dialysis against deionized/distilled water to remove excess salts and acetic acid. Then the preparation was frozen to maximize the surface area to volume ratio, and finally the frozen preparation was freeze-dried.

If desired, trehalose at a final concentration of 1% can be added to the collagen solution prior to freeze-drying to facilitate stabilization of the freeze-dried collagen preparation. The freeze-dried collagen preparation should optimally be added to individual containers, such that each container holds from 10 to 20 mg of collagen. Finally, the individual containers are vacuum evacuated and sealed so that the collagen carrier/matrix remains sterile.

The ground demineralized bone powder was obtained by impact fragmentation, and the bone particles were freeze-dried. Next the bone particles were sized using mesh sieves, and a particle size range of 250 to 710 millimicron was chosen. Then the sized demineralized bone powder was divided into 25 mg samples and placed into individual vials and the vials were then vacuum evacuated and sealed in order to insure sterility.

At the time of usage, the freeze-dried collagen carrier/matrix was reconstituted by the sterile addition of 0.5 ml of sterile isotonic saline. The freeze-dried demineralized bone powder was reconstituted by sterile addition of 0.3 ml of sterile isotonic saline. To complete formulation of the composite material, the reconstituted collagen carrier/matrix was transferred to the vial containing the reconstituted demineralized bone powder.

The resulting composite material preferably includes 1% to 2% collagen matrix and 50% demineralized bone powder in a total volume of approximately 1 ml. The preparation may have the consistency of a viscous liquid or paste, depending on the desires of the individual preparing the formulation and the intended application(s). This method of preparation of facilitates the addition of optional compounds should such additions be desired.

EXAMPLE IV

An additional modification of the composite material, collagen carrier/matrix and demineralized bone powder can be accomplished by addition of the freeze-dried collagen carrier/matrix of the freeze-dried demineralized bone powder prior to packaging, vacuum evacuation, and preparation for long-term storage. Optional compounds can be added prior to freeze-drying and this method of formulation facilitates reconstitution prior to clinical applications.

What is claimed:

1. A non-immunogenic composition for the promotion of allogenic bone growth and repair in an individual, comprising:

demineralized human bone powder, and type-I telopeptide containing human collagen.

2. A non-immunogenic composition for the promotion of allogenic bone growth and repair in an individual, comprising:

demineralized human bone powder, and type-I telopeptide containing human collagen, wherein said human bone powder and said human collagen are derived from the same human cadaver source.

3. The non-immunogenic composition of claim 2, wherein said human collagen is derived from tendons and ligaments of said human.

4. The non-immunogenic composition of claim 2, wherein said type-I telopeptide containing human collagen comprises about 0.25 to 40.00 weight percent of said non-immunogenic composition.

5. The non-immunogenic composition of claim 2, wherein said type-I telopeptide containing human collagen is produced by the process, comprising:

extracting said collagen from said human cadaver source in dilute acid to produce extracted collagen;

precipitating said extracted collagen from said acid solution to produce precipitated collagen; and washing said precipitated collagen to form washed collagen.

6. The non-immunogenic composition of claim 5, wherein said dilute acid comprises one or more dilute organic acids.

7. The non-immunogenic composition of claim 6, wherein said dilute organic acid has a pH of from 3 to 4.

8. The non-immunogenic composition of claim 6, wherein said dilute organic acid is one or more member selected from the group consisting of: acetic acid, lactic acid, malic acid, citric acid, glutaric acid, and proprionic acid.

9. The non-immunogenic composition of claim 8, wherein said dilute organic acid is acetic acid.

10. The non-immunogenic composition of claim 5, wherein said process further comprises the steps of:

resolubilizing said washed collagen to form resolubilized collagen, and dialyzing said resolubilized collagen against isotonic saline to form dialyzed collagen.

11. The non-immunogenic composition of claim 10, wherein said steps of washing, resolubilizing, and dialyzing, are cyclically repeated from 2 to 6 times.

12. The non-immunogenic composition of claim 11, wherein said demineralized human bone powder comprises about 20 to 90 weight percent of said non-immunogenic composition.

13. The non-immunogenic composition of claim 12, wherein said demineralized human bone powder comprises about 30 to 50 weight percent of said non-immunogenic composition.

14. The non-immunogenic composition of claim 13, wherein said demineralized human bone powder has a particle size of from about 125 microns to about 2 millimeters.

15. The non-immunogenic composition of claim 14, wherein said demineralized human bone powder has a particle size of from about 125 microns to about 500 microns.

16. The non-immunogenic composition of claim 14, wherein said demineralized human bone powder has a particle size of from about 250 microns to about 710 microns.

17. The non-immunogenic composition of claim 14, wherein said demineralized bone powder has a particle size of from about 710 microns to about 2 millimeters.

18. The non-immunogenic composition of claim 2, wherein said non-immunogenic composition is flowable and injectable, and is a gel or a paste.

19. The non-immunogenic composition of claim 2, further comprising:

one or more elements selected from the group consisting of: a bioactive compound, an antibiotic, an antiviral agent, an antitumor agent, an immunosuppressant agent, a permeation enhancer, a nucleic acid, a mesenchymal element, a gelation enhancing compound and autogenously derived osteoblast cells.

20. The non-immunogenic composition of claim 19, wherein said bioactive compound is one or more members selected from the group consisting of: bone morphogenetic protein, transforming growth factor β, fibroblast growth factor, insulin, and platelet derived growth factor.

21. The non-immunogenic composition of claim 19, wherein said antibiotic is penicillin.

22. The non-immunogenic composition of claim 19, wherein said antiviral agent is a detergent or a peroxide generating agent.

23. The immunogenic composition of claim 22, wherein said detergent is one or more members selected from the group consisting of: Triton X-100, sodium dodecyl sulfate, Nonidet P-40, and Brij-35.

24. The non-immunogenic composition of claim 19, wherein said immunosuppressant agent is bovine intestinal choline phosphatase.

25. The non-immunogenic composition of claim 19, wherein said permeation enhancer is one or more fatty acid esters.

26. The non-immunogenic composition of claim 25, wherein said fatty acid ester is a mono ester of polyethylene glycol selected from the group consisting of: laureate, myristate and stearate.

27. The non-immunogenic composition of claim 19, wherein said gelation enhancing compound is a glycosanine glycan selected from the group consisting of: hyaluronic acid, chondroitin sulfate and dermatin sulfate.

* * * * *